United States Patent
Höijer et al.

(10) Patent No.: US 6,954,671 B1
(45) Date of Patent: Oct. 11, 2005

(54) IMPLANTABLE HEART STIMULATOR OR WHICH IDENTIFIES THE ORIGIN OF HEART SIGNALS

(75) Inventors: Johan-Carl Höijer, Malmö (SE); Martin Obel, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 09/980,179

(22) PCT Filed: May 25, 2000

(86) PCT No.: PCT/SE00/01073

§ 371 (c)(1),
(2), (4) Date: Apr. 12, 2002

(87) PCT Pub. No.: WO00/72916

PCT Pub. Date: Dec. 7, 2000

(30) Foreign Application Priority Data

May 28, 1999 (SE) .................................. 9901966

(51) Int. Cl.$^7$ ............................................. A61N 1/18
(52) U.S. Cl. ............................................ 607/9
(58) Field of Search ............................ 607/14, 5, 9

(56) References Cited

U.S. PATENT DOCUMENTS

| | | | |
|---|---|---|---|
| 4,305,396 A | 12/1981 | Wittkampf et al. | |
| 4,880,004 A | 11/1989 | Baker, Jr. et al. | |
| 5,350,402 A | 9/1994 | Infinger et al. | |
| 5,755,739 A | * | 5/1998 | Sun et al. ............. 607/14 |

FOREIGN PATENT DOCUMENTS

| | | |
|---|---|---|
| EP | 0 646 390 | 4/1995 |
| EP | 0 917 887 | 5/1999 |

* cited by examiner

*Primary Examiner*—George Manuel
*Assistant Examiner*—Dana D. Greene
(74) *Attorney, Agent, or Firm*—Schiff Hardin LLP

(57) ABSTRACT

An implantable heart stimulator has a heart signal detector adapted to detect electrical heart signals and to apply the detected signals to at least two detection channels. Each detection channel includes a filter, with each filter having a passband that differs from the passband of the other filters. Each channel also includes a threshold detector and a peak amplitude determining unit connected to the output of the filter in that channel. A heart event identifying unit is connected to the outputs of each channel and unambiguously identifies a type of signal which produced a detected heart event by applying predetermined identifying criteria to the outputs of the threshold detector and the peak amplitude determining unit from each channel.

6 Claims, 2 Drawing Sheets

IMPLANTABLE HEART STIMULATOR OR WHICH IDENTIFIES THE ORIGIN OF HEART SIGNALS

BACKGROUND OF THE INVENTION

1. Field of the Invention

The present invention relates to an implantable heart stimulator, e.g. a pacemaker or a defibrillator.

2. Description of the Prior Art

In conventional pacemaker technology often a single band-pass filter is used in the sensing circuit of the pacemaker in order to detect electrical heart signals. When using this known technique the origin of a signal that caused a sensed event is difficult to determine.

A ventricular event occurring early in the heart cycle (prior to a normally timed QRS-complex) and arising from a focus in the ventricles is often referred to as a premature ventricular contraction (PVC).

If a PVC not is detected due to undersensing it can cause inappropriately timed, asynchronous or competitive stimulation pulses to be delivered. Undersensing is defined as a failure of the pacemaker to sense an electrical signal related to a heart event, e.g. a PVC, due to the sensitivity of the sensing circuit of the pacemaker being set too low. This can often be corrected by programming the pacemaker to a more sensitive setting, i.e. decreasing the value of the sensitivity level.

U.S. Pat. No. 4,880,004 discloses an implantable cardiac stimulator for detecting and treating cardiac arrhythmias. The stimulator includes a sense amplifier responsive to sensed cardiac signals for detecting and distinguishing normal and abnormal cardiac activity within the sensed signals. The sense amplifier includes an automatic gain control amplifier, a filter and a comparator having a pair of signal channels for processing the sensed signals according to different frequency bandpass characteristics to establish sensing thresholds, margins and signal gain. One of the signal channels constitutes a feedback loop for determining the signal gain and the sensing margin for the other channel.

In U.S. Pat. No. 5,350,402 an atrial defibrillator is disclosed including a first detector for detecting R-waves of the heart and a second detector for detecting T-waves of the heart. The detection criterion is based on a predetermined time interval relationship between the R-wave and the T-wave. According to a software implementation of the T-wave detector, a microprocessor may be implemented for filtering the output of a sense amplifier with a high-pass filter and a low-pass filter. The derivative of the filtered signal is calculated by discrete differentiation of the filtered data and the derivative is re-filtered with a low-pass filter. These values are used in further calculations to determine if a T-wave is detected.

In U.S. Pat. No. 5,755,739 an adaptive and morphological system for discriminating P-Waves and R-waves inside the human body is disclosed. A drawback of a system using morphological recognition is that it probably is not fast enough for real time operation and that it is often implemented by a microprocessor that has unacceptably high energy consumption.

In U.S. Pat. No. 4,305,396 an improved automatically rate adaptive pacemaker is disclosed. The theory behind this patent is that a correlation has been identified between e.g. the amplitudes of the R-wave and T-wave and the heart rate. This correlation is then used to control a rate-responsive pacemaker. The peak values of the QRS-wave and T-wave, respectively, are detected in detection windows using conventional techniques. The detected values are then applied to a correlation block where a rate-controlling signal is generated.

European Application 0 917 887 discloses a cardiac event detecting system for an implantable heart stimulator intended to be connected to the heart of a patient via at least two unipolar electrode leads, or at least one bipolar electrode lead having one electrode pole in the atrium and one electrode pole in the ventricle, for sensing heart signals. This system has at least two signal channels for signals sensed between the two electrode poles and between one of the electrode poles and the stimulator capsule, respectively.

European Application 0 646 390 discloses a heart stimulator having an atrial electrode in an atrium of a heart and a ventricular electrode in a ventricle in the heart. In order to sense stimulated events in the heart a detector is connected between the atrial and ventricular electrodes to measure electrical heart signals between them.

SUMMARY OF THE INVENTION

An object of the present invention is to improve the safety in detecting electrical heart signals and to make it possible to determine the origin of detected signals. The heart stimulator according to the invention is in particular useful for a safe detection of premature ventricular contractions (PVCs).

Another object of the invention is to arrange an implantable heart stimulator having a detection of electrical heart signals that is fast and low energy consuming.

The above objects are achieved in accordance with the principles of the present invention in an implantable heart stimulator having at least one heart signal detector adapted to detect electrical signals originating from either a ventricle or an atrium, at least two detection channels connected to the detector, each channel including a filter with a predetermined filter characteristic, a threshold detector with a predetermined threshold, and peak amplitude determining unit. In each detection channel, the filter therein generates a filtered signal that is supplied to the threshold detector, which emits a detection signal if the filtered signal exceeds the threshold, and the filtered signal is also supplied to the peak amplitude determining unit which generates a signal representing the peak amplitude value of the filtered signal.

Each of the detection channels is connected to the same cardiac lead electrode, and each filter has a passband that is different from the passband of the other filters. Each of the channels is continuously active, and the respective signals therefrom are supplied to a heart event identifying unit that unambiguously identifies the type of signal that caused a detected heart event by applying predetermined heart event identifying criteria to the detection channel signals.

DESCRIPTION OF THE PREFERRED EMBODIMENTS

Figure 1:
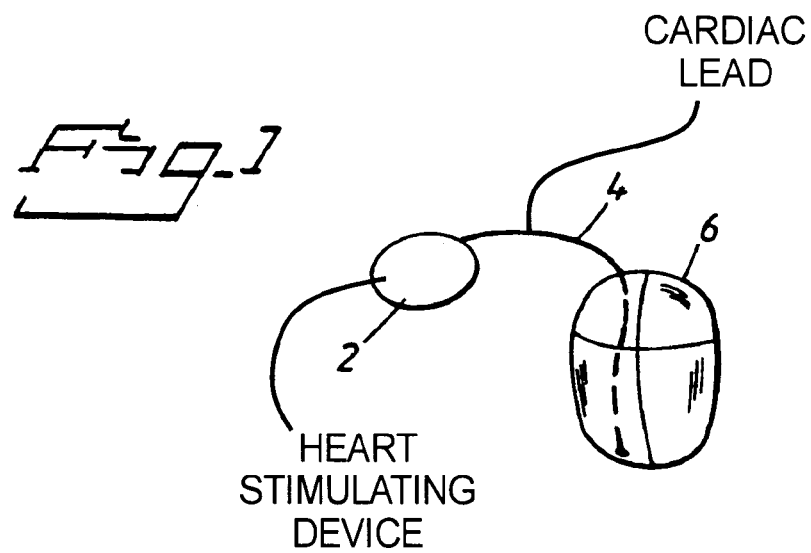
FIG. 1 shows an implantable heart stimulator.

FIG. 1 shows an implantable heart stimulator formed by a heart stimulating device 2 and an electrode lead 4 inserted into the ventricle of a heart 6. The electrode lead 4 is inserted into the heart 6 and arranged in the ventricle according to procedures well known to persons skilled in the art. The heart stimulator in FIG. 1 relates to a single chamber heart stimulator, which means that the electrode lead is arranged in one chamber of the heart, in this case the right ventricle. However, it should be noted that the invention is equally applicable in a dual chamber heart stimulator that has two heart electrode leads adapted to stimulate the heart both in the atrium and in the ventricle, as well as in a multi-chamber heart stimulator adapted to stimulate three or four chambers of the heart.

Figure 2:
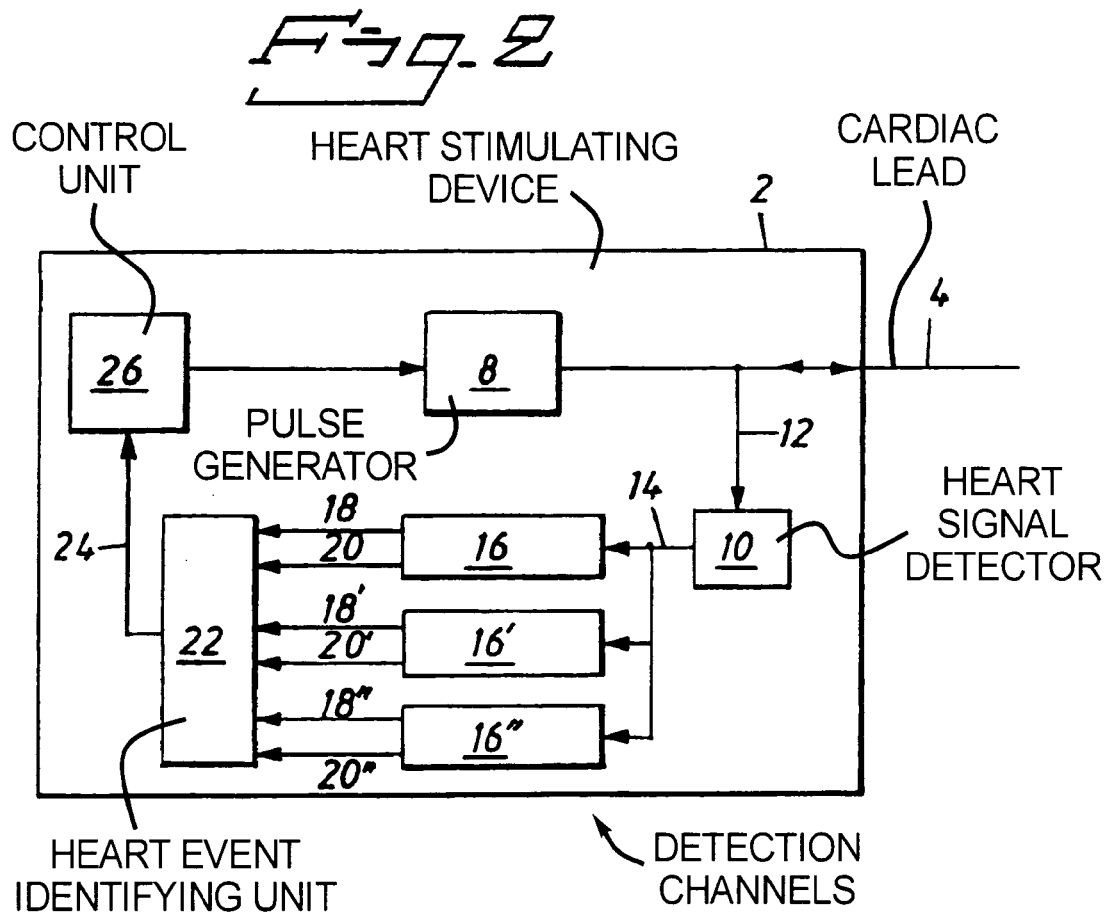
FIG. 2 is a block diagram of the implantable heart stimulating device according to the invention.

FIG. 2 illustrates the implantable heart stimulating device 2 according to the invention, that has a pulse generator 8 for generating heart stimulating pulses to the heart via the electrode lead 4. The heart stimulating device 2 further has a heart signal detector 10 connected to the electrode lead 4 and adapted to receive electrical heart signals 12 and to generate detected electrical heart signals 14 to three detection channels 16, 16', 16". Each channel is adapted to generate a detection signal 18, 18', 18" and a peak amplitude value 20, 20', 20" to a heart event identifying unit 22 that generates a signal 24 that identifies a detected heart event and applies the signal 24 to a control unit 26.

Figure 3:
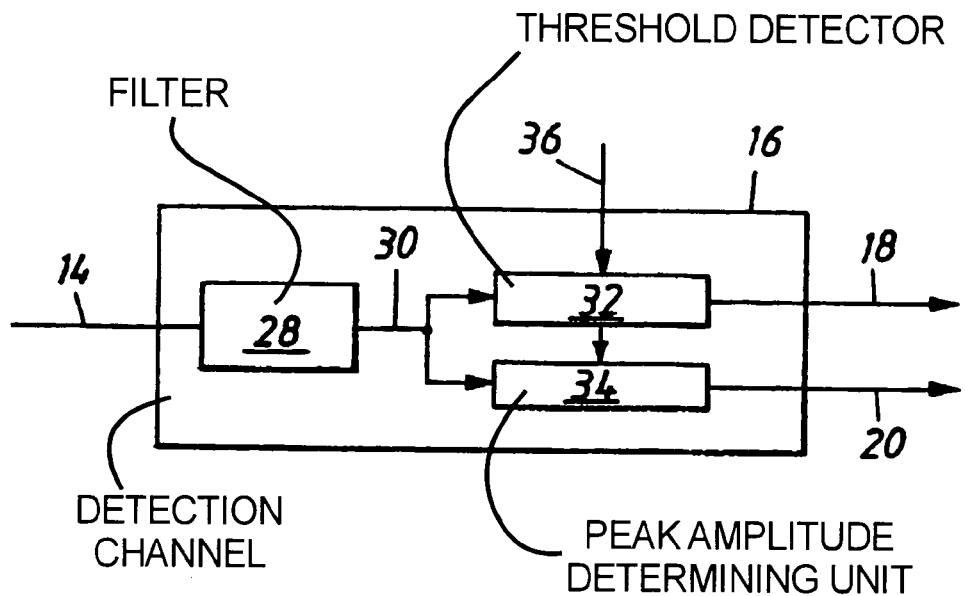
FIG. 3 is a block diagram of a detection channel according to the invention.

FIG. 3 illustrates one of the detection channels 16. The detection channel 16 has a filter 28 that generates a filtered signal 30 that is applied to a threshold detector 32 and to a peak amplitude determining unit 34. If the filtered signal exceeds a predetermined threshold 36 of the threshold detector 32 the detection signal 18 is generated. The peak amplitude determining unit 34 generates the peak amplitude value 20.

The invention is described in relation to a single chamber heart stimulator, i.e. with one electrode lead placed in the atrium or in the ventricle of the heart. As mentioned above the invention is equally applicable in a dual chamber heart stimulator where, for each electrode lead, a heart signal detection means and at least two detection channels are associated.

Each filter 28 has a predetermined filter characteristic, that differs from that of the filter 28 in another each of the other detection channels.

If the heart signal detector 10 receives signals detected in the ventricle of the heart, the predetermined respective filter characteristics of the filters 28 in three parallel detection channels are e.g. tuned to be sensitive to R-waves, T-waves and PVCs.

The filter 28 sensitive to R-waves is a band-pass filter with a passband in the range 20–50 Hz.

The filter 28 sensitive to T-waves is a band-pass filter with a passband in the range 2–10 Hz.

And the filter 28 sensitive to PVCs is a band-pass filter with a passband typically in the range 15–40 Hz.

If the heart signal detector 10 instead receives signals detected in the atrium of the heart, the predetermined respective filter characteristics of the filters 28 in two parallel detection channels preferably are tuned to be sensitive to P-waves and far-field R-waves. The filter 28 sensitive to P-waves is a band-pass filter with a narrow passband around 30 Hz.

The filter 28 sensitive to far-field R-waves is a band-pass filter with a pass-band typically in the range 10–35 Hz.

It is however possible to arrange further detection channels both for detection in the atrium and in the ventricle, e.g. to be able to detect different kinds of arrhythmia, states of atrial or ventricular fibrillation etc.

The filter filters 28 can be implemented using digital or analog filter techniques.

If a digital filter technology is used the analog detected heart signal is A/D converted before filtering is performed, and the processing of the filtered signal in the threshold detector 32 and in the peak amplitude determining unit 34 is digital.

If an analog filter instead is used the above-mentioned processing might also be performed in an analog threshold detector and in an analog peak amplitude determining means. As an alternative the filtered signal is A/D-converted after the filtration and then applied to the threshold detector 32 and the peak amplitude determining unit 34.

The filter characteristics discussed above could either be set at the time of manufacture of the implantable device or could be set by a physician during implantation of the device or later at a follow-up visit. The filters 28 can be automatically tuned by tuning means in the heart event identifying unit 22.

Figure 4:
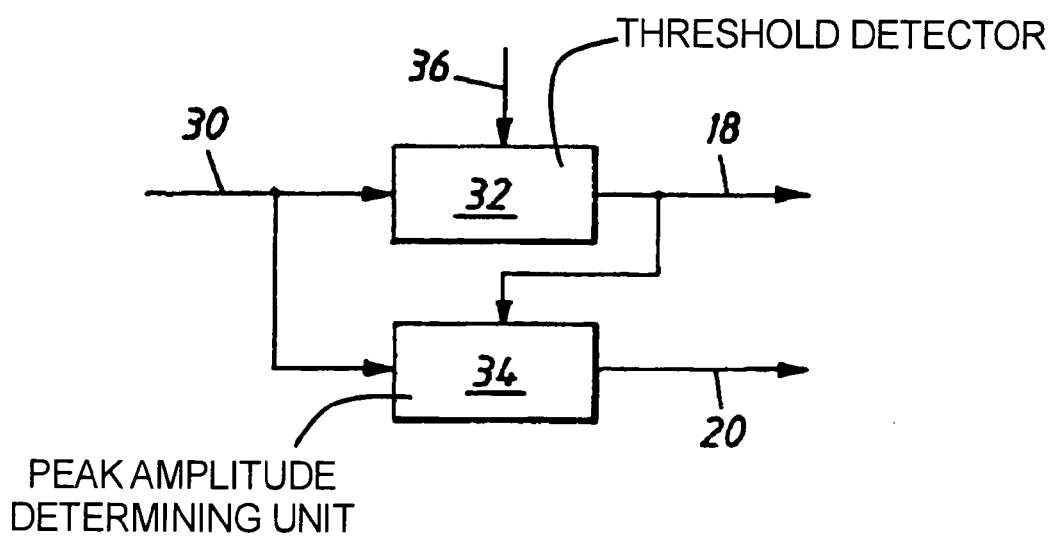
FIG. 4 is a block diagram of a preferred embodiment of a part of a detection channel according to the invention.

FIG. 4 illustrates a preferred embodiment of the threshold detector 32 and the peak amplitude determining unit 34. The filtered signal 30 is a stream of digital bits representing the heart signal. The bit-stream is applied to the threshold detector 32 which is a digital comparator with a threshold 36 that generates the detection signal 18 if the filtered signal exceeds the threshold 36. The detection signal is applied to the peak amplitude determining unit 34 that, according to this embodiment, is a shift register. When a detection signal is received by the determining unit 34, the digital bit-stream is clocked into the shift register during a predetermined time, about 10–30 ins. When the predetermined time has elapsed, the content of the shift register is inspected in order to find the maximum value and that value is then generated as the peak amplitude value 20.

According to another preferred embodiment of the invention the heart signal detector 10 receives signals detected in the ventricle of the heart. In FIG. 2 the detection channel 16 is tuned to be sensitive to R-waves, the detection channel 16' is tuned to be sensitive to T-waves and the detection channel 16" is tuned to be sensitive to PVCs. The detection channel 16 generates detection signal 19 ($R_{det}$), indicating a detected R-Wave, and a peak amplitude value 20 ($R_{max}$) indicating the peak amplitude of the detected R-wave. According to the same principles $T_{det}$, $T_{max}$, $PVC_{det}$ and $PVC_{max}$ are generated by the detection channels 16', 16", respectively.

The detection signals and the peak amplitude values are received by the heart event identifying unit 22 where a number of heart event identifying criteria are applied.

To unequivocally identify an R-wave the following criteria must be fulfilled:

Detection signal $R_{det}$ received, i.e. no $T_{det}$ or $PVC_{det}$, and $R_{max}/PVC_{max}>1$ (also $R_{max}/T_{max}>1$ could be checked).

The division $R_{max}/PVC_{max}$ need only be performed if there also was a $PVC_{det}$.

$R_{max}-PVC_{max}>0$ can be used instead of $R_{max}/PVC_{max}>1$.

To unequivocally identify a PVC the following criteria must be fulfilled: Detection signal $PVC_{det}$ received, i.e. no $R_{det}$ or $T_{det}$ and $PVC_{max}/R_{max}>1$ and $PVC_{max}/T_{max}>1$ if $PVC_{det}$ and $R_{det}$.

The division $PVC_{max}/R_{max}$ need only be performed if there also was an $R_{det}$.

$PVC_{max}-R_{max}>*$ can be used instead of $PVC_{max}/R_{max}>1$.

Typical values for $R_{max}$ is in the range of 6–12 mV and for $PVC_{max}$ is in the range of 3–6 mV. $T_{max}$ has a maximal peak amplitude below 1 mV.

According to a second preferred embodiment of the invention the heart signal detector 10 receives signals detected in the atrium of the heart. In FIG. 2 only two detection channels are used and the detection channel 16 is tuned to be sensitive to P-waves and the detection channel 16' is tuned to be sensitive to far field R-waves. The detection channel 16 generates detection signal 18 ($P_{det}$), indicating a detected P-Wave, and a peak amplitude value 20 ($P_{max}$) indicating the peak amplitude of the detected P-wave. According to the same principles R (far-field)$_{det}$ and R(farfield)$_{max}$ are generated by the detection channel 16'.

To unequivocally identify a P-wave, the following criteria must be fulfilled:

Detection signal $P_{det}$ received and $P_{max}$/R(far-field)$_{max}$>1 if $P_{det}$ and R(far-field) $_{det}$.

To unequivocally identify a far-field R-wave the following criteria must be fulfilled:

Detection signal R(far-field)$_{det}$ received and R(far-field) $_{max}$/$P_{max}$/>1 if R(far-field) $_{det}$ and $P_{det}$.

Typical values for $P_{max}$ when filtered with the P-wave adapted filter 28 is in the range of 3–4 mV and when filtered with the far-field R-wave adapted filter 28 in the range of 2–3 mV. Typical values for R(far-field)$_{max}$ when filtered with the P-wave adapted filter is in the range of 2–3 mV and when filtered with the far-field R-wave adapted filter 28 in the range of 3–4 mV.

It should be noted that the individual variability regarding signal amplitudes may be significant.

The heart event identifying unit 22 is implemented either by software in a microprocessor or by a digital network using commonly available programming technique or digital network design.

The filters 28 are continuously active which means that each filter 28 in each of the detection channels 16, 16' and 16" receives detected electrical heart signals and performs filtering during the whole heart cycle.

As soon as a detection signal is received by the heart event identifying unit 22, the peak amplitude values received during a predetermined time interval, e.g. from * to 30 ms, are used in the above-mentioned identifying criteria to identify the detected heart event.

The signal 24 identifying a detected heart event is applied to the control unit 26 where appropriate action is taken in response of the detected heart event. Such action could be a resetting of certain time intervals, a change of mode of operation for the heart stimulator and/or the adjustment of certain parameters, e.g. the sensitivity level. All these actions are well known to a person skilled in the art of heart stimulators and therefore need not be further described in the present application.

According to still another embodiment of the invention the heart event identifying unit 22 is provided with means for tuning and adjusting each filter 28 to be more sensitive to the heart event it is intended to detect, e.g. R-waves. That could be done by e.g. changing the band-width or another filter parameter of the filter.

In the embodiments of the invention described above the heart signal detection technique is only briefly discussed. It should be noted that any detection technique resulting in a detection of heart signals is applicable in the present invention. The heart signal can be detected by a single bipolar electrode lead by measuring between a tip and a ring electrode surfaces. If instead a unipolar heart electrode is used detection is performed between a tip electrode surface and an electrode surface at the pacemaker housing. Still another possibility is to detect between electrode surfaces at different electrode leads that could be unipolar, bipolar or multipolar. The above-mentioned measurement techniques and expressions are well known to a person skilled in the art of heart stimulators and are therefore not further described.

Although modifications and changes may be suggested by those skilled in the art, it is the intention of the inventors to embody within the patent warranted hereon all changes and modifications as reasonably and properly come within the scope of their contribution to the art.

What is claimed is:

1. An implantable heart stimulator comprising:
   a heart signal detector connected to a cardiac lead having an electrode adapted to detect electrical a heart signal originating from either a ventricle or an atrium;
   at least two detection channels connected to said heart signal detector for receiving said electrical heart signal from said electrode;
   each of said detection channels comprising a bandpass filter which emits a bandpass filtered signal at a filter output, a threshold detector which compares said bandpass filtered signal to a threshold and which generates a threshold detector output signal if said bandpass filtered signal exceeds said threshold, and a peak amplitude determining unit connected to the output of said bandpass filter which generates a peak amplitude value of said bandpass filtered signal;
   the respective bandpass filters in said at least two detection channels having different passbands from each other, and each of said detection channels being continuously active; and
   a heart event identifying unit connected to the threshold detector and the peak amplitude determining unit in each of said detection channels which unambiguously identifies, by applying predetermined heart event identifying criteria to the threshold detector output and the peak amplitude value from each of said detection channels, a type of the electrical heart signal detected by said heart signal detector.

2. An implantable heart stimulator as claimed in claim 1 wherein said heart event identifying unit employs heart event identifying criteria selected from the group consisting of a quotient of respective peak amplitude values from two of said detection channels and a difference between respective peak amplitude values from two of said detection channels.

3. An implantable heart stimulator as claimed in claim 1 comprising three of said detection channels, said three detection channels containing respective filters with respective filter characteristics tuned to be sensitive to R-waves, T-waves and PVCs.

4. An implantable heart stimulator as claimed in claim 1 comprising three of said detection channels, and wherein the respective bandpass filters in said three detection channels have respective passbands tuned to be sensitive to P-waves, a premature atrial contraction and far-field R-waves.

5. An implantable heart stimulator as claimed in claim 1 wherein said heart event identifying unit comprises a tuner control connected to the respective bandpass filters in said at least two detection channels for tuning said respective bandpass filters.

6. An implantable heart stimulator as claimed in claim 1 wherein said heart event identifying unit employs identifying criteria for identifying types of electrical heart signals selected from the group consisting of R-waves, T-waves, premature ventricular contractions, P-waves, and far-field R-waves.

* * * * *